(12) United States Patent
Modi

(10) Patent No.: US 9,308,268 B2
(45) Date of Patent: *Apr. 12, 2016

(54) SOLUBILIZED BENZOYL PEROXYDE ACNE

(75) Inventor: Pankaj Modi, Ancaster, CA (US)

(73) Assignee: TRANSDERMAL CORP, Birmingham, MI (US)

( * ) Notice: Subject to any disclaimer, the term of this patent is extended or adjusted under 35 U.S.C. 154(b) by 626 days.

This patent is subject to a terminal disclaimer.

(21) Appl. No.: 12/803,543

(22) Filed: Jun. 29, 2010

(65) Prior Publication Data

US 2011/0027382 A1  Feb. 3, 2011

Related U.S. Application Data

(63) Continuation-in-part of application No. 11/057,481, filed on Feb. 14, 2005, now Pat. No. 7,838,011, and a continuation-in-part of application No. 12/133,939, filed on Jun. 5, 2008, now abandoned.

(51) Int. Cl.
| | |
|---|---|
| A61K 47/24 | (2006.01) |
| A61K 9/00 | (2006.01) |
| A61K 9/107 | (2006.01) |
| A61K 31/327 | (2006.01) |
| A61K 38/39 | (2006.01) |
| A61K 45/06 | (2006.01) |

(52) U.S. Cl.
CPC ............... *A61K 47/24* (2013.01); *A61K 9/0014* (2013.01); *A61K 9/107* (2013.01); *A61K 9/1075* (2013.01); *A61K 31/327* (2013.01); *A61K 38/39* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,874,074 A | * | 2/1999 | Smith | ......................... 424/78.02 |
| 6,017,520 A | * | 1/2000 | Synodis et al. | ............. 424/78.02 |
| 2003/0077301 A1 | * | 4/2003 | Maibach et al. | ............... 424/400 |

* cited by examiner

*Primary Examiner* — Gary Nickol
*Assistant Examiner* — Khatol Shahnan Shah

(57) ABSTRACT

The invention relates to a novel solubilized benzoyl peroxide topical formulation for the treatment of acne comprising: benzoyl peroxide, one or more micelle forming compounds, one or more skin penetration enhancers, a surfactant, and one or more solvents, wherein the benzoyl peroxide is solubilized in the solvent. The invention further relates to the use of the topical formulation as well as the process for making the topical formulation.

34 Claims, 4 Drawing Sheets

FIG. 1

Topical BP: Acne
Pilot Clinical Study

Results:

- After 8 weeks or less treatment the mean reductions from baseline in non inflammatory and inflammatory lesion count, were 66% and 69% with this novel formulation in comparison with placebo where improvement was 3.7% and 5.2%
- At week 4, more than 80% of patients had maintained a 50% or greater global improvement from baseline, and more than 40% had maintained a 75% or greater global improvement.

FIG. 2

Topical BP: Acne
Pilot Clinical Study

Results:

Overall disease severity score mean ± SD 3.7±1.7
Mean percentage (%) change in papules and pustules

| Baseline | week 1 | week 2 | week 4 | week 6 | week 8 |
|----------|--------|--------|--------|--------|--------|
| 0 | 7.5 | 15.1 | 27.7 | 40.1 | 56.3 |

Incident of >50% global improvement from baseline 21/26
Incident of >75% global improvement from baseline 14/26
% change non-inflammatory lesions counts 64±22.2
% change inflammatory lesions count 67±27.3

Clinical Photographs

Insoluble Peroxide

Solubolized peroxide

SOLUBILIZED BENZOYL PEROXYDE ACNE

PRIORITY

THIS APPLICATION CLAIMS THE PRIORITY OF AND IS A CONTINUATION IN PART OF U.S. patent application Ser. No. 11/057,481 FILED Feb. 14, 2005, NOW U.S. Pat. No. 7,838,011 AND U.S. patent application Ser. No. 12/133,939 FILED Jun. 5, 2008.

FIELD

The present invention relates to a solubilized small molecule topical formulation for the transdermal application of the small molecule agent and a method of formulation.

BACKGROUND OF THE INVENTION

Acne vulgaris ("acne") is a disorder resulting from the action of hormones on the skin's oil glands (sebaceous glands), wherein the sebaceous glands of the skin produce excess sebum, and become enlarged and/or infected when the pore opening becomes plugged with a comedo (a mixture of keratin and sebum). The symptoms of acne include plugged pores and outbreaks of inflamed lesions commonly called pimples.

The pathophysiology of acne vulgaris, the most common cutaneous disease, is the consequence of the interplay of follicular hyperkeratinization, bacteria in the follicular canal, and sebum production. The exact mechanism triggering the development of the comedone and the stimuli causing the non-inflamed lesion to become provoked are poorly understood. The microbiology of acne vulgaris and its immunologic ramifications constitute a major thrust of present research in the elucidation of the pathogenesis of inflammatory acne. Within the microbial flora of the pilosebaceous unit, *P. acnes* is the most meaningful organism in acne causation.

The methods of acne therapy are usually grouped into several categories such as keratolytics, antibacterials, sebosuppressives, and hormones. Benzoyl peroxide (also referred to as "BP") is the most widely used topical agent for acne since its introduction in the 1960's. BP is very effective for the treatment of acne because it is antibacterial, functions as a peeling agent, has comedolytic activity, and reduces free fatty acid levels. Concomitant topical treatment of BP and erythromycin is stated to be superior to BP alone. However, no synergistic activity has been found with this combination. Instead, such combination therapies are hypothesized to gain their efficacy by the coupled action of two effective treatments.

Acne lesions usually occur on the face, neck, back, chest, and shoulders. It is the most common skin disease amongst teenagers and young adults. Acne can occur at any age, and is common to all ethnic backgrounds. Nearly 85 percent of people between the ages of 12 and 24 develop this disorder. For most people, acne tends to go away by the time they reach their thirties. However, some people in their forties and fifties continue to have acne, commonly termed "adult acne".

Several acne treatments are commercially available, such as those in the following categories, for example: topical bactericidals (e.g. triclosan, chlorhexidine gluconate and benzoyl peroxide); topical antibiotics (e.g. erythromycin, tetracycline and clindamycin); oral antibiotics (e.g. tetracyclines and trimethoprim); hormonal treatments (e.g. hormonal contraception in females); topical retinoids (e.g. tretinoin, adapalene and tazarotene); oral retinoids (e.g. isotretinoin, marketed as Accutane®, Roche Pharmaceuticals, N.J.); and phototherapy.

Many of the over-the-counter ("OTC") acne medications currently marketed rely on chemicals which have an antibacterial and/or a peeling/drying action which aids in breaking down keratin (i.e. keratolytic agent), thus helping to clear plugged pores.

Consequently, there are a wide variety of drugs that are used in topical formulations for the treatment of acne, and there are disadvantages in respect of each drug or combination of drugs. Benzoyl peroxide, resorcinol, salicylic acid, and sulfur are among the most common topical OTC agents used to treat acne. Benzoyl peroxide has an antibacterial effect and also acts as a peeling and drying agent, increasing cell turnover and helping to clear plugged pores.

In general, topical formulations used to treat acne must be water-based, as oil-based formulations can cause or further aggravate acne eruptions.

Benzoyl peroxide is a crystalline solid with a melting point of 103° C. to 106° C., and is insoluble in water.

Benzoyl peroxide is soluble in organic solvents, but most organic solvents are toxic and therefore not suitable for pharmaceutical/cosmetic use. Polar organic solvents such as acetone and ethanol are less toxic, but the flammability of these solvents as well as the ability of these solvents to irritate and strip the skin of its protective mantle limit their use in pharmaceutical or cosmetic compositions.

A common method of treating acne vulgaris is to treat the skin with a benzoyl peroxide dispersion of crystals in a gel/lotion/cream base. However, the use of essentially undissolved benzoyl peroxide crystals has limited efficacy, and consequently requires high concentrations of benzoyl peroxide to be effective. Furthermore, it is difficult for the benzoyl peroxide crystals to penetrate into the comedone and into the sebaceous gland itself, because the comedone plug is a physical barrier and the size of the follicular opening is limited.

One method and formulation which was proposed in U.S. Pat. No. 7,326,420 ("'420 patent") which is described as increasing the efficacy of peroxides such as benzoyl peroxide in the treatment of skin conditions such as acne relates to methods of increasing radicals formed by peroxides on/in the skin, more specifically near/in the comedone (but not limited thereto), for topical use in dermatology. The methods use the radicals formed by peroxides such as benzoyl peroxide, optimizing conditions such that the skin/comedone is the only place they are formed as opposed to in a storage container or wherever the benzoyl peroxide happens to be from the time of application to when the benzoyl peroxide breaks down into its radicals or is metabolized.

The methods described in the '420 patent may use the principles of photodynamic therapy directed at acne. Instead of forming radicals in cancer cells, the methods form radicals in/by the comedone (skin surface, sebum within *P. acnes*). The methods use the assumption that radicals derived from BP or other peroxides are the most useful in acne therapy (as opposed to reactive oxygen intermediates used in photodynamic therapy).

In a specific embodiment, the '420 patent relates to the use of transitional metals such as Cu(1) and ferrous ions to increase the efficacy of peroxides such as benzoyl peroxide. It is asserted that such an addition to benzoyl peroxide would increase the generation of benzoyloxyl radicals.

In a further example, U.S. Pat. No. 6,117,843 ("'843 patent") asserts that it provides novel acne treatment compositions comprising both clindamycin, an antibiotic effective against Propionibacterium acnes, and benzoyl peroxide, a keratolytic and desquamative agent which further possesses a broad antibacterial activity. The two agents are combined in a Pharmaceutically acceptable fluid carrier, usually a gel, which has been found to provide effective topical treatment of acne. The benzoyl peroxide will be present in the carrier at a concentration from 1% by weight to 20% by weight and the clindamycin will be present at a concentration from 0.2% by weight to 4% by weight. By maintaining the compositions at a pH below 7, the tendency of benzoyl peroxide to oxidize and degrade clindamycin is largely overcome and the product remains stable during storage at room temperature for extended periods, typically several months or longer. Additionally, the compositions of the '843 patent are asserted to have been found to remain substantially odor free even after storage at room temperature for extended periods.

Additional instances wherein benzoyl peroxide is employed are described in U.S. Pat. No. 4,497,794, discloses compositions combining erythromycin and benzoyl peroxide for the treatment of acne, as described above. Other patents disclosing the combination of erythromycin and benzoyl peroxide for acne treatment and other purposes include U.S. Pat. No. 4,411,893; U.S. Pat. No. 4,692,329; and British Patent No. 1,594,314. The combination of erythromycin with other organic peroxides for the treatment of acne is described in British Patent No. 2,088,717. Other formulations containing benzoyl peroxide for the treatment of acne are described in U.S. Pat. Nos. 3,535,422, 4,056,611; 4,318,907; 4,923,900; 4,387,107; and 4,228,163. Other peroxide formulations for treating acne are described in U.S. Pat. No. 4,607,101. The use of clindamycin and other lincomycin antibiotics for the treatment of acne is described in U.S. Pat. No. 3,969,516. Hirschmann (1988) Arch. Dermatol. 124:1691-1700 and Fulton, Jr., et al. (1974) Arch. Dermatol. 110:83-86 describe the topical use of antibiotics for the treatment of acne.

Consequently, commercially available topical formulations of benzoyl peroxide have several disadvantages, since they: (1) have a limited ability to penetrate the skin and consequently have low efficacy for the dose administered; (2) cannot be formulated as clear compositions and sprays; and (3) leave an aesthetically undesirable white, powder residue on the skin once the topical formulation dries.

Relatively little progress has been made in reaching the target of safe and effective non-invasive transdermal delivery of formulations for macromolecules, including peptides and proteins. Barriers to developing transdermal formulations for proteins, peptides and other large and small molecules include poor intrinsic permeability, cellular enzymatic degradation and chemical instability. Pharmaceutical approaches to address these barriers that have been successful with traditional small, organic drug molecules have not readily translated into effective peptide and protein formulations. The ability of molecules to permeate the skin effectively appears to be related to molecular size, lipid solubility and peptide protein ionization. Molecules less than 1000 daltons appear to cross the skin barriers rapidly. As molecular size increases, the permeability of the molecule decreases rapidly. Lipid soluble compounds are more permeable than non-lipid soluble molecules. Maximum absorption occurs when molecules are un-ionized or neutral in electrical charges. Charged molecules, therefore, present the biggest challenges to absorption through the skin.

Some enhancers, especially those related to bile salts, and some protein solubilizing agents are extremely potent in transporting the molecules effectively across the tight junctions and skin. Several approaches have been utilized to improve the transport of the bile salt-based delivery systems, including the use of protease inhibitors and various polymer matrices. Other attempts to deliver large molecules using single bile acids or enhancing agents in combination with protease inhibitors and biodegradable polymeric materials similarly failed to achieve therapeutic levels of proteinic drugs in the patient. Single enhancing agents fail to loosen tight cellular junctions for the time needed to permit passage of large molecules through the skin membranes without further degradation.

Various transmission systems have been proposed in connection with the delivery of small molecules such as local anesthetic compounds. U.S. Pat. No. 5,013,545 to Blackmon et. al. discloses aqueous gel-containing topical medications comprising high concentrations of alcohol, water and topically effective amounts of a pharmaceutical active such as hydrocortisone, diphenhydramine hydrochloride, lidocaine or miconazole nitrate in a gel matrix primarily consisting of water-soluble carboxyvinyl polymers. A gel clarifying agent may be optionally added for aesthetic reasons.

U.S. Pat. No. 4,937,078 to Mezie et. al. discloses the incorporation of certain concentrations of topical anesthetic actives into liposomes which are of a substantially greater size than nano particles. U.S. Pat. No. 5,081,158 to Pomerantz discloses the use of medicated protective films as a carrier for topical anesthetics. The films are comprised of hydroxypropyl cellulose (HPC) and an esterification agent which renders the HPC soluble in a non-volatile solvent such as ethanol, isopropanol or methanol. Medicinal compounds such as benzocaine and a variety of other topical anesthetics, antibiotics and steroids are incorporated which, when applied to the skin, result in situ formed medicated films from which the actives are released to provide a sustained supply of the medicine at the treatment site.

U.S. Pat. No. 5,002,974 to Geria discloses a topical anesthetic and skin moisturizing composition comprising any one of a number of topical anesthetics, including pramoxine, in an oil-in-water emulsion including a dissolved surface active agent. The composition is asserted to provide an aesthetically pleasing analgesic skin care product. The emulsion not only provides relief from the pain associated with irritated skin but is asserted to soften and moisturize the skin with an oily coating. U.S. Pat. No. 4,493,591 to Fourman et al discloses skin care cosmetic formulations comprised of a cellulosic polymer/solvent system capable of dispersing thin, substantive films upon the skin. Such films may serve as a carrier for sun blocking agents and insect repellents and also serve to prevent water loss form the skin surface to the environment.

Finally, U.S. Pat. No. 4,389,418 to Burton et. al., in a more general and traditional sense, discloses the use of hydrocarbons such as petrolatum, paraffin wax and ozokerite and other emollients as skin moisturizing materials. These function by covering the skin with a hydrophobic occlusive film which prevents water loss from the skin to the environment.

SUMMARY

In one aspect, this patent application discloses a solubilized benzoyl peroxidetopical formulation that comprises benzoyl peroxide, one or more solvents, one or more skin penetration enhancers, and a surfactant.

The Mixed Micellar Small Molecule ("MMSM") delivery system addresses the above need by providing an improved delivery of pharmaceutical compositions comprising a macromolecular pharmaceutical agent, an alkali metal alkyl sulfate, a pharmaceutically acceptable edetate, an alkali metal salicylate and at least one additional micelle-forming compound, in a suitable solvent. The agent can be one or more proteins, peptides, hormones, vaccines or drugs. The molecular weight of the macromolecular pharmaceutical agent preferably ranges between about 1,000 and 2,000,000 daltons. The agent is presented in micellar form, with a micelle size of approximately one to 10 nanometers (nm).

As used herein the term "mixed micelles" refers to at least two different types of micelles, each of which has been formed using different micelle forming compounds; for example, the present compositions comprise a mix of at least two different types of micelles—micelles formed between the pharmaceutical agent and alkali metal alkyl sulfate, and micelles formed between the pharmaceutical agent and at least one different additional micelle forming compound as disclosed herein. It will be understood that each individual micelle can be formed from more than one micelle forming compound as well. The mixed micelles of the present invention tend to be smaller than the pores of the membranes (skin). It is therefore believed that the extremely small size of the present mixed micelles helps the encapsulated macromolecules penetrate efficiently through the skin. Thus, the present compositions offer increased bioavailability of active drug, particularly across the skin, when compared with pharmaceutical preparations known in the art.

The MMSM delivery system also enhances the rate of absorption of macromolecular pharmaceutical agents comprising the agent in combination with an alkali metal alkyl sulfate, a pharmaceutically acceptable edetate, at least one alkali metal salicylate, and at least one micelle-forming compound.

The MMSM delivery system is a pharmaceutical composition comprising of: an effective amount of a macromolecular pharmaceutical agent; an alkali metal alkyl sulfate; a pharmaceutically acceptable edetate; at least one alkali metal salicylate; at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof, and a suitable solvent. The alkali metal alkyl sulfate, the edetate, and the alkali metal salicylate are each present in a concentration between about 1 and 20 wt./wt. % of the total composition, each micelle-forming compound concentration is between about 1 and 20 wt./wt. % of the total composition, and the total concentration of the alkali metal alkyl sulfate, edetate and the micelle-forming compound together is less than 50 wt./wt. % of the total composition.

The solubilized benzoyl peroxide topical formulation may comprise one or more solvents that are selected from ethylene glycol-400 (low molecular weight solvent), propylene or butylene glycol, isopropyl or ethyl alcohol, short chain alkyl esters, or combinations thereof.

The solubilized benzoyl peroxide topical formulation may comprise the surfactant sodium lauryl sulfate. The solubilized benzoyl peroxide topical formulation may comprise the skin penetration enhancer dimethylsulfoxide (DMSO).

In a preferred embodiment, the solubilized benzoyl peroxide topical formulation comprises: benzoyl peroxide, the skin penetration enhancer dimethylsulfoxide (DMSO), the surfactant sodium lauryl sulfate and the solvents: ethylene glycol-400, propylene or butylene glycol and isopropyl or ethyl alcohol.

In another embodiment, this patent application discloses the use of the solubilized benzoyl peroxide topical formulation for the treatment and/or prophylaxis of acne.

In a further embodiment, this patent application discloses a process for the preparation of the solubilized benzoyl peroxide topical formulation.

The solubilized benzoyl peroxide topical formulation may include additional ingredients to form an emulsion, suspension, cream, lotion, get or stick for topical administration.

BRIEF DESCRIPTION OF THE DRAWINGS

Embodiments of the invention will be described, by way of example only, with reference to the appended drawings, wherein:

FIGS. 1 And 2 are a topical pilot clinical study;

DETAILED DESCRIPTION

Figure 3:
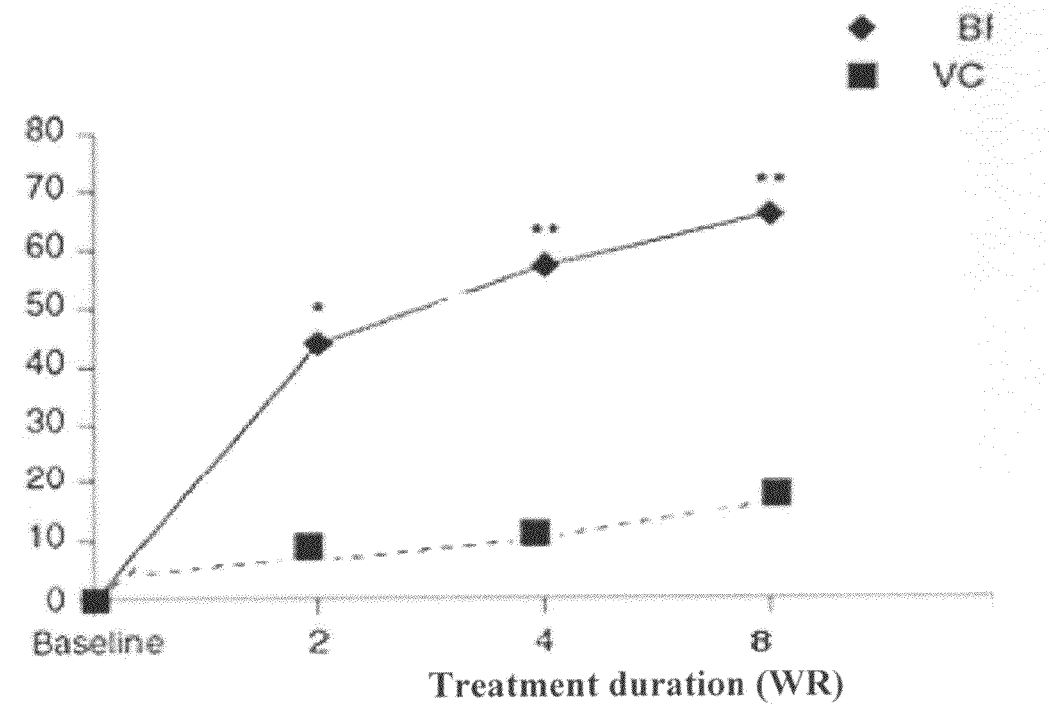
FIG. 3 is a chart of the inflammatory lesion reduction.

The present invention generally provides for the manufacture and use of formulations of solubilized benzoyl peroxide. The solubilized benzoyl peroxide formulations provide a solvent vehicle for the treatment of acne and comprise solubilized benzoyl peroxide molecules that are available to penetrate into follicles, follicle oil glands, the stratum corneum and the epidermis of the skin. The solubilized benzoyl peroxide saturates the targeted infected areas to destroy the bacteria-causing acne.

The solubilized benzoyl peroxide topical formulation comprises: benzoylperoxide, a solvent, a skin penetration enhancer, and a surfactant.

Definitions

In describing and claiming the present invention, the following terminology will be used in accordance with the definitions set forth below.

The singular forms "a," "an," and "the" include plural referents unless the context clearly dictates otherwise. Thus, for example, reference to "a solvent" includes reference to one or more of such solvents, and reference to "the dispersant" includes reference to one or more of such dispersants.

As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with a one or a plurality of agents in order to provide a desired composition. Those of ordinary skill in the art will recognize a number of carriers that are well known for making specific remedial compositions.

As used herein, "biologically acceptable carrier" refers to a material which is suitable for use in connection with a particular biological material. A biologically acceptable carrier is compatible with, and does not adversely affect, a biological material or subject contacted therewith under prescribed conditions.

As used herein, "cosmetic" is an adjective referring to improving the appearance of a surface or covering defects.

Typically, cosmetic compositions can be used to improve aesthetic rather than functional aspects of a surface. Most commonly, cosmetic compositions are formulated for application as a beauty treatment or for affecting personal appearance of the body, for example, natural tooth enamel and dental veneer surfaces.

As used herein, "remedial" is an adjective referring to remedying, correcting, treating, improving, or preventing an undesirable condition. A remedial composition can therefore be formulated to remove undesirable stains from the surface of natural tooth enamel or veneer. Similarly, remedial compositions can be configured to remove, prevent or minimize formation of undesirable elements such as stain build up and the like.

As used herein, "biological material" refers to any material which is a product of a biological organism. Typical biological materials of interest can include organic oils and the like.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of 1 to 5 should be interpreted to include not only the explicitly recited limits of 1 and 5, but also to include individual values such as 2, 2.7, 3.6, 4.2, and sub-ranges such as 1-2.5, 1.8-3.2, 2.6-4.9, etc. This interpretation should apply regardless of the breadth of the range or the characteristic being described, and also applies to open-ended ranges reciting only one end point, such as "greater than 25," or "less than 10".

The term "volatile component" as used herein refers to a component (e.g., a solvent or combination of solvents) that changes readily from solid or liquid to a vapor, e.g., that evaporates readily at some temperature at or below body temperature and less readily at room temperature, such as a component that evaporates rapidly between 21 and 37.degree. C. at atmospheric pressure.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the term "saturation" refers to the point at which a solution of a substance (e.g., a local anesthetic agent) can dissolve no more of that substance and additional amounts of it will appear as a precipitate. The phrase "near saturation" refers to a solution which is at least 90% saturated, such as 90%, 91%, 92%, 93%, 94%, 95%, 96%, 97%, 98%, or 99% saturated. The phrase "above saturation" refers to a solution which has a higher concentration of substance (e.g., a local anesthetic agent) than the concentration at which the solution is saturated (e.g., it is greater than 100% saturated).

The drug delivery system and methods of the present invention may be utilized to treat an individual in need thereof. In certain embodiments, the individual is a mammal such as a human, or a non-human mammal The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The formulations of the present invention can be administered to a subject topically, for example, as a gel, foam, solution, lotion, cream, ointment or spray applied to the skin.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the anesthetic agent which produces an anesthetic effect.

The formulations of the present invention for topical or transdermal administration include powders, sprays, ointments, pastes, creams, lotions, gels, solutions, patches and inhalants. The anesthetic agent may be mixed under sterile conditions with the other components of the drug delivery system, and with any preservatives, buffers, or propellants that may be required.

The formulations of the present invention may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like.

Actual dosage levels of the active ingredients in the formulations may be varied so as to obtain an amount of the active ingredient that is effective to achieve the desired anesthetic response for a particular patient, composition, and mode of administration, without being toxic to the patient.

The selected dosage level will depend upon a variety of factors including the activity of the particular agent or combination of agents employed, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the formulation required. For example, the physician or veterinarian could start doses of the formulations at levels lower than that required in order to achieve the desired anesthetic effect and gradually increase the dosage until the desired effect is achieved. By "therapeutically effective amount" is meant the concentration of the agent that is sufficient to elicit the desired effect. It is generally understood that the effective amount of the agent will vary according to the weight, sex, age, and medical history of the subject. Other factors which influence the effective amount may include, but are not limited to, the severity of the patient's condition, the disorder being treated, the stability of the agent of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference). As used herein, the term "macromolecular", when used in conjunction with the term pharmaceutical agent, refers to pharmaceutical agents having a molecular weight greater than about 1000 daltons; preferably the macromolecular pharmaceutical agents of the present invention have a molecular weight between about 1000 and 2,000,000 daltons although even larger molecules are also contemplated.

The macromolecular pharmaceutical agent exists in micellar form in its intact pharmaceutical composition. A micelle is a colloidal aggregate of amphipathic molecules in which the polar hydrophilic portion of the molecules extends outwardly while the non-polar hydrophobic portion extends inwardly. The micelle encapsulates the molecule of interest. As discussed below, various combinations of micelle-forming compounds are utilized in order to achieve the present formulation. It is believed that the presence of the micelles significantly aids in the absorption of the macromolecular pharmaceutical agent both because of their enhanced absorption ability, and also because of their size. The particle size of the micelles will typically be in the range of 1 to 10 nanometers. Preferably, the micelle size ranges between 1 and 5 nanometers.

The following definitions apply herein: "About" means approximately or nearly and in the context of a numerical value or range set forth herein means 10% of the numerical value or range recited or claimed.

"Local administration" means direct administration of a pharmaceutical at or to the vicinity of a site on or within an animal body, at which site a biological effect of the pharmaceutical is desired. Local administration excludes systemic routes of administration, such as intravenous or oral administration. Topical administration is a type of local administration in which a pharmaceutical agent is applied to a person's skin. Topical administration of a neurotoxin, such as botulinum toxin, excludes systemic administration of the neurotoxin. In other words, and unlike conventional therapeutic transdermal methods, topical administration of botulinum toxin does not result in significant amounts, such as the majority of, the neurotoxin passing into the circulatory system of the patient.

"Enhancing agent" refers to an agent that enhances the permeability of a patient's skin so that the benzoyl peroxide can be absorbed by the skin to achieve a therapeutic effect. In reference to the disclosure herein, enhancing agent specifically includes dimethylsulfoxide (DMSO) or a combination of pluronic lecithin organizer (PLO) and DMSO. An enhancing agent may include, and is not limited to, alcohols, such as short chain alcohols, long chain alcohols, or polyalcohols; amines and amides, such as urea, amino acids or their esters, amides, AZONE®, derivatives of AZONE®, pyrrolidones, or derivatives of pyrrolidones; terpenes and derivatives of terpenes; fatty acids and their esters; macrocyclic compounds; tensides; or sulfoxides other than dimethylsulfoxide, such as, decylmethylsulfoxide; liposomes; transfersomes; lecithin vesicles; ethosomes; water; surfactants, such as anionic, cationic, and nonionic surfactants; polyols; and essential oils.

Substances that facilitate the absorption or transport of large molecules (>1000 daltons) across biological membranes are referred to in the art as "enhancers" or "absorption aids." These compounds include chelators, bile salts, fatty acids, synthetic hydrophilic and hydrophobic compounds, and biodegradable polymeric compounds. Many enhancers lack a satisfactory safety profile respecting irritation, lowering of the barrier function, and impairment of the mucociliary clearance protective mechanism.

Benzoyl Peroxide

Benzoyl peroxide is normally commercially available as either pure crystals or in a wet crystalline state. Either of these or other forms of benzoyl peroxide can be mixed with the solvents described below to form the solubilized benzoyl peroxide topical formulation.

Due to the increased skin penetration of the benzoyl peroxide of the solubilized benzoyl peroxide topical formulation, the minimum effective amount of benzoyl peroxide can be lower than the amount of benzoyl peroxide used in presently available acne formulations containing benzoyl peroxide.

Thus, for example, a solubilized benzoyl peroxide topical formulation containing 5% benzoyl peroxide has 2 to 3 times the skin penetration than prior art 10% benzoyl peroxide compositions.

The amount of benzoyl peroxide solubilized in the solvent will vary depending on a number of factors, including, for example, the desired activity of benzoyl peroxide, the ultimate form of the product, and the particular solvent employed. The benzoyl peroxide will constitute from 0.5 to 70% benzoyl peroxide by weight, preferably from 1 to 30% benzoyl peroxide by weight, more preferably from 1 to 10% benzoyl peroxide by weight, and most preferably from 2 to 5% benzoyl peroxide by weight of the solubilized benzoyl peroxide topical formulation.

Micelle Forming Compounds

The compositions of the MMSM delivery system further comprise at least one micelle-forming compound selected from the group comprising lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof.

Each micelle-forming compound listed above is present in the composition in a concentration of between about 1 and 20 wt./wt. % of the total composition. More preferably, each micelle-forming compound is present in a concentration of between about 1 and 5 wt./wt. % of the total composition. The alkali metal alkyl sulfate functions as a micelle forming agent, and is added to the composition in addition to the one or more other micelle-forming compounds listed herein. The total concentration of alkali metal alkyl sulfate, the edetate and the micelle-forming compounds together is less than 50 wt./wt. % of the total composition.

The lecithin can be saturated or unsaturated, and is preferably selected from the group consisting of phosphatidylcholine, phosphatidylserine, sphingomyelin, phosphatidylethanolamine, cephalin, and lysolecithin and mixtures thereof. Saturated and unsaturated lecithin are commercially available from The American Lecithin Co. as Phospholipon-H™ and Phospholipon-G™, respectively.

Preferred salts of hyaluronic acid are alkali metal hyaluronates, especially sodium hyaluronate, alkaline earth hyaluronates, and aluminum hyaluronate. When using hyaluronic acid or pharmaceutically acceptable salts thereof in the present compositions, a concentration of between about 1 and 5 wt./wt. % of the total composition is preferred, more preferably between about 1.5 and 3.5 wt./wt. %.

In the preferred embodiments of the delivery system, at least two micelle-forming compounds are used. The micelle-forming compound combination is selected from the group consisting of i) sodium hyaluronate and saturated phospholipid, ii) lecithin and sodium hyaluronate, iii) sodium hyaluronate and evening of primrose oil, iv) saturated phospholipid and glycolic acid, v) saturated phospholipid, glycolic acid and lactic acid, vi) sodium hyaluronate, oleic acid and gamma linoleic acid, and vii) trihydroxy oxocholanyl glycine, lecithin and chenodeoxycholate.

An isotonic agent such as glycerin or dibasic sodium phosphate may also be added after formation of the mixed micellar composition. The isotonic agent serves to keep the micelles in solution. When glycerin is used as one of the micelle-forming compounds it will also function as an isotonic agent. When dibasic sodium phosphate is used it will also serve to inhibit bacterial growth.

The pH of the present pharmaceutical composition should typically be in the range of 5 to 8, more preferably 6 to 7. Hydrochloric acid or sodium hydroxide can be utilized to adjust the pH of the composition as needed.

Solvents

Solvents useful for solubilizing benzoyl peroxide and preparing the solubilized benzoyl peroxide topical formulation include, alone or in combination, for example: ethylene glycol-400 (low molecular weight solvent), propylene or butylene glycol, isopropyl or ethyl alcohol, short chain alkyl esters, ethers, aldehydes, ketones or alcohols of benzoic acid, benzyl alcohol, phenol or phathalic acid, aryl esters, ethers, alcohols of benzyl alcohol, alkyl esters of salicylic acid, alkyl esters of phenol, alkyl esters of phthalic acid, alkyl ethers of benzyl alcohol, alkyl esters of phthalic acid, alkyl ethers of benzyl alcohol, alkyl ethers of phenol, benzoyl benzoate, benzoyl alcohol, diethyl phthalate, benzoic acid 2-phenyl ethyl ester, methyl salicylate, ethyl salicylate, propyl salicylate, butyl salicylate, ethyl benzoate, methyl benzoate, propyl benzoate, butyl benzoate, dimethyl phthalate, diethyl phthalate, benzyl ethyl ether, benzyl methyl ether, phenetole, phenyl acetone, phenyl ethyl alcohol, phenoxyethanol, phenyl acetaldehyde, ethyl phenyl acetate, phenyl methyl ketone, phenyl acetate, benzyl acetate, benzyl aceto acetate, benzyl formate, benzyl alcohol, ethyl benzyl alcohol, phenyl benzoate, phenyl ether, benzyl benzoate, and phenyl ethyl ester.

Preferred solvents are ethylene glycol-400 (low molecular weight solvent), propylene or butylene glycol, isopropyl or ethyl alcohol, and short chain alkyl esters.

The amount of solvent used to solubilize the benzoyl peroxide will vary depending on a number of factors, including, for example, the ultimate form of the product and the particular solvent employed. Generally, the solvent will constitute from 1 to 70 percent, by weight, of the solubilized benzoyl peroxide topical formulation.

Skin Penetration Enhancers

Skin penetration enhancers promote the absorption of an active ingredient by the skin. One or more skin penetration enhancers may be used to facilitate the permeation of benzoyl peroxide through the patient's skin.

Examples of skin penetration enhancers include, but are not limited to, dimethylsulfoxide (DMSO), alcohols (such as short chain alcohols, long chain alcohols, or polyalcohols), amines and amides (such as urea, amino acids or their esters), AZONE® (including derivatives of AZONE®), pyrrolidones (including derivatives of pyrrolidones), terpenes (including derivatives of terpenes), fatty acids and their esters, macrocyclic compounds, tensides, sulfoxides (including decylmethylsulfoxide), liposomes, micelles, transfersome, lecithin vehicles, ethosomes, surfactants (such as anionic, cationic, and nonionic surfactants), essential oils, d-limonene, *Quillaja saponaria* (QTS), *Acanthophyllum squarrusom* (ATS), allantoin, fulvic acid, myrrh, Eldopaque and/or hydroquinone glyquin A preferred skin penetration enhancer is DMSO. The concentration of DMSO can range from 0.5 to 8%, and preferably from 1 to 4% by weight of the solubilized benzoyl peroxide topical formulation.

Surfactants

The solubilized benzoyl peroxide topical formulation also contains one or more surfactants.

Suitable surfactants include both naturally occurring compounds as well assynthetic surfactants. Examples of suitable surfactants include: phospholipids and cholates, polysorbates (i.e. fatty acid esters of polyethoxylated sorbitol), polyethylene glycol esters of fatty acids from sources such as castor oil, polyethoxylated fatty acids (e.g. stearic acid), octylphenolpoly(ethyleneglycolether), polyethoxylated isooctylphenol/formaldehyde polymer, poloxamers (e.g. poly(oxyethylene)-poly(oxypropylene) block copolymers), polyoxyethylene fatty alcohol ethers, polyoxyethylene nonylphenyl ethers, polyoxyethylene isooctylphenol ethers, SDS, phospholipids (e.g. phosphatidylcholines (lecithins), including soy or egg lecithin), phosphatidylglycerol, phosphatidylinositol, phosphatidylserine, phosphatidic acid, cardiolipin, and phosphatidylethanolamine.

Mixtures of surfactant molecules, including mixtures of surfactants of different chemical types, are acceptable. Surfactants should be suitable for cosmetic or pharmaceutical administration and compatible with benzoyl peroxide.

A preferred surfactant is sodium lauryl sulfate. The concentration of sodium lauryl sulfate can range from 0.5 to 8%, and preferably from 1 to 4% by weight of the 30 solubilized benzoyl peroxide topical formulation.

Additional Components

Various other ingredients can optionally be included in the solubilized benzoyl peroxide topical formulation, such as: topical anesthetics (e.g. benzocaine, lidocaine, tetracaine, prilocaine), antibiotics/antimicrobials/bactericidals/anti-fungals (including dermatologically acceptable salts of tetracyclin and tetracyclin derivatives, gentamycin, kanamycin, streptomycin, neomycin, capreomycin, lincomycin, paromomycin, tobramycin, erythromycin, triclosan, antimicrobial peptides, octopirox, parachlorometa xylenol nystatin, tolnaftate, miconazole hydrochloride, chlorhexidine gluconate, chlorhexidine hydrochloride, methanamine hippurate, methanamine mandelate, minocycline hydrochloride, clindamycin, cleocin, (3-lactam derivatives such as aminopenicillin and mixtures thereof), 1 to 2% sodium hydroxide, salicylic acid, and other medicinal ingredients in amounts effective for the treatment of acne.

Skin Lightening agents or scar removing agents such as Hydroquinone, Hydrogen Peroxide, Kombuchka, Tri and Pentatpetides like Matrixyl and Metrixyl 3000, Witch Hazel Extract, Grape seed extracts, green tea extracts, turmeric extracts etc in combination with Sodium Hyaluronate and Collagen etc can be included.

The solubilized benzoyl peroxide topical formulation can be added to other ingredients to form desired products, including: serums, toners, pumps or aerosol sprays, clear gels, sticks, creams, lotions and mousses, solutions, emulsions (including microemulsions), suspensions, creams, lotions, gels, sticks, powders, or other typical solid or liquid compositions used for treatment of skin. Such compositions may also contain cooling, solvent constituents and other ingredients typically used in such products, such as moisturizers and hydration agents, preservatives, emulsifiers, natural or synthetic oils, surfactants, detergents, gelling agents, emollients, antioxidants, fragrances, fillers, thickeners, waxes, odor absorbers, dyestuffs, coloring agents, powders, viscosity-controlling agents and water, and optionally including anti-itch actives, botanical extracts, conditioning agents, darkening or lightening agents, glitter, humectants, mica, minerals polyphenols, silicones or derivatives thereof, sun blocks, vitamins, and phytomedicinals, and combinations thereof, for example.

When preparing desired products (e.g., emulsions, lotions, creams or gels) the solubilized benzoyl peroxide topical formulation can be added to other ingredients to form desired products at low temperatures (e.g. 25 to 40° C.). In these processes, since benzoyl peroxide is never in contact with substantial heat, the possibility of decomposition or fire is greatly reduced.

Suitable suspending agents include the following constituents, for example: polyacrylamide, C13-14 isoparaffin & laureth 7; C13-14 isoparaffin, mineral oil, polyacrylate, polyacrylamide and ethoxylated sorbitan ester; acrylamide/sodium acryloyldimethyl taurate copolymer, isohexadecane and ethoxylated sorbitan ester; and combinations thereof.

In some emulsions, the aqueous phase constituting the dispersion medium may include any suitable surfactant, humectant, suspending agent, and/or buffer systems, and combinations thereof suitable for combining with benzoyl peroxide. Examples of suitable humectants include glycerin; however any material capable of obtaining moisture may be added provided it is stable with benzoyl peroxide.

Preparation of the Solubilized Benzoyl Peroxide Topical Formulation

The solubilized benzoyl peroxide topical formulation is prepared by combining the one or more micelle forming compounds, one or more solvents, one or more skin penetration enhancers, and surfactant and stirring at a temperature between 25 to 40° C. The combination of these ingredients results in the formation of micelles. Benzoyl peroxide is then added to the solution with continuous stirring to form the solubilized benzoyl peroxide topical formulation.

The solubility of benzoyl peroxide in the solvent(s) offers an improved method for preparing anhydrous benzoyl peroxide without subjecting the composition to any heat during processing. For example, when benzoyl peroxide-wet crystals containing 25% water are mixed with one or more solvents, the solvents (which solubilize the benzoyl peroxide) replace water in the process of changing the crystalline benzoyl peroxide into a solution, and the water can be readily separated.

In contrast to prior art formulations of benzoyl peroxide, the benzoyl peroxide will actively go into solution at levels as high as 10% by weigh of the solubilized benzyl peroxide topical formulation. Furthermore, the solubilized benzoyl peroxide topical formulation is translucent and has increased efficacy.

If levels of benzoyl peroxide are desired that exceed the solubility parameters of the solvent(s), then a saturated solution of fine soft benzoyl peroxide slurry is formed. This composition can then be filtered to remove the water from the composition, thereby providing a fine textured, substantially water reduced benzoyl peroxide paste/saturated solution composition.

The examples which follow are intended to illustrate specific embodiments of the invention.

Example 1

Formulation Method A

The following solvents and additional ingredients are combined:

100 mL Ethylene Glycol-400 (low molecular weight colvent)
100 mL Propylene or Butylene Glycol
10-20 mL Isopropyl or Ethyl Alcohol
1% Sodium Lauryl Sulfate
1% DMSO
1% NaOH solution
1%-5% wt/wt micelle forming compound Heat the above solution to 30-35 C. with constant stirring.

Add Benzoyl Peroxide powder (5% by wt or 3.5% by wt).

The following components can also be added, if desired: 2-8% wt of colloidal sulfur, 2% salicylic acid, 2% resorcinol or phenol, 3% glycerin and 2% benzocaine and 2% tetracaine dissolved in 20 mL ethyl alcohol to the above solution at 30-35 C. and stir the solution for 45 minutes.

The result is a homogenous milky solution without any gritty feeling. Cool the solution to room temperature, and add 20 mL of hydrogen peroxide solution (3%). The following ingredients may be added a s needed to produce a lotion: water (as needed), 20 mL (3%-5% hydrogen peroxide), glyceryl stearate, PEG-100 stearate, cetearyl alcohol, dimethicone, panthenol, allantoin, carbomer, ceteareth-20, xanthan gum, triethanolamine, fragrance (parfum), diazolidinyl urea, methylparaben, propylparaben.

The resultant emulsion or clear solution or gel has been found to be stable at room temperature for at least one year.

Formulation Method B a) mixing a macromolecular pharmaceutical agent in a suitable solvent with an alkali metal alkyl sulfate, an edetate, and an alkali metal salicylate;

b) subsequently adding at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof, to form a micellar macromolecular pharmaceutical agent composition; and, c) after step b), adding at least one additional micelle-forming compound which is different from that added in step b) but selected from the same group. Preferably, the micelle-forming compound selected in step b) is lecithin.

Again, during or after step b), a phenolic compound as described above can be added to the composition. Mixing can be vigorous or not. Vigorous mixing may be accomplished by using high-speed stirrers, such as magnetic stirrers, propeller stirrers, or sonicators, and is preferred.

The particle size of the micelles will typically be in the range of 1 to 10 nanometers. Preferably, the micelle size ranges between 1 and 5 nanometers.

Example 2

In-Vitro Percutaneous Absorption of Solubilzed Benzoyl Peroxide Topical Formulation Materials and Methods Transdermal absorption of the solubilized benzoyl peroxide topical formulation of Example 1 containing radiolabelled benzoyl peroxide (using 1-125) was measured over a 24 hour period in human cadaver skin using the Franz in vitro diffusion chamber.

A 5% benzoyl peroxide topical formulation of the invention was applied onto the human cadaver cell uniformly with gentle rubbing for 1 min. Every 3 hours the percent of benzoyl peroxide recovered in the stratum corneum, epidermis, and stratum corneum surface was determined by calculating the percent recovery of the total amount of benzoyl peroxide applied from the bottom of the diffusion chamber. The total micrograms of benzoyl peroxide recovered from each location was calculated by measuring the radioactivity counts using a scintillation counter. Over the 24 hour study period, approximately 77% of the benzoyl peroxide applied penetrated the skin as shown in Table 1 below.

TABLE 1

Total dose applied; 5 mg (5000 microgram) on 5 cm area

| Time | Percentage of Benzoyl Peroxide Recovered |
|---|---|
| 0 | 0 |
| 2 | 7 |
| 4 | 11 |
| 7 | 15 |
| 10 | 33 |
| 15 | 54 |
| 20 | 67 |
| 22 | 77 |

Example 3

A Comparison of Patterns of Deposition of Two Formulations of Benzoyl Peroxide on Skin: Scanning Electron Micrograph on Silicone Wafer×500

A dramatic change in the magnitude of benzoyl peroxide solubility occurred above a dielectric constant value of about 20. The solubility of this drug can be enhanced by the replacement of a polar solvent by a vehicle of lower dielectric constant. A stable submicron emulsion gel was made with cremophor EL, glycerol, caprylic-capric triglycerides, and water in the proportion of 20-20/35/25, respectively; 3.5% benzoyl peroxide was also added. This submicron emulsion vehicle consisted of oil droplets, with a mean diameter of approximately 100-150 nm, dispersed in a continuous water phase.

These studies confirm the potential of benzoyl peroxide incorporation into a submicron emulsion gel and the stability of this formulation.

FIG. 1 shows a prior art unsolubilized benzoyl peroxide formulation (gritty formulation) on human skin at a magnification of 500×. FIG. 2 shows the solubilized benzoyl peroxide topical formulation of Example 1 on human skin at a magnification of 500×.

The results of this study demonstrated that the solubilized benzoyl peroxide topical formulation is distributed evenly over the surface of the skin, and lacks the gritty, granular appearance of the prior art benzoyl peroxide formulations.

Example 4

Human Clinical Studies (Before and After Photographs)

Objective:

To assess acne improvement and tolerability of the solubilized benzoyl peroxide topical formulation of Example 1 (at 3.5% benzoyl peroxide) during 12 weeks of treatment in comparison to a non-medicated cream control.

Participants:

A total of 99 patients aged 12 to 39 years with facial acne were enrolled in the study.

Intervention:

The study was randomized, and controlled by using a non-medicated (vehicle) cream identical to the base of the active cream. The medication samples were distributed in identical boxed pairs of 30 g tubes labeled "morning application" and "evening application". The dosage of cream per application was approximately 0.6 g, described and demonstrated to patients as a pea-sized amount. Patients were requested to maintain diary records in which they recorded treatment periods of all applications. Clinical assistants collected these records at each visit. Patients were seen at baseline, defined as the visit when treatment was initiated, and again at 2, 4, 8, and 12 weeks of treatment.

Photography:

During each visit, front and bilateral 45° side facial views of every patient were taken using a platform-mounted 35-mm SLR camera system (Nikon Corp, Tokyo, Japan) with a fixed-magnification 60-mm lens (f2.8) (Nikkor; Nikon Corp) and a dual-point light system (Twinflash; Canfield Scientific, Inc, Fairfield, N.J.). Patients were positioned in a stereotactic device designed to capture registered serial photographs using standardized subject angles, framing, lighting, exposure, and reproduction ratio.

Main Outcome Measures:

Efficacy was based on reduction in acne lesions, treatment success (50%-100% improvement in global response to treatment) and improvement in overall disease severity.

Figure 4:
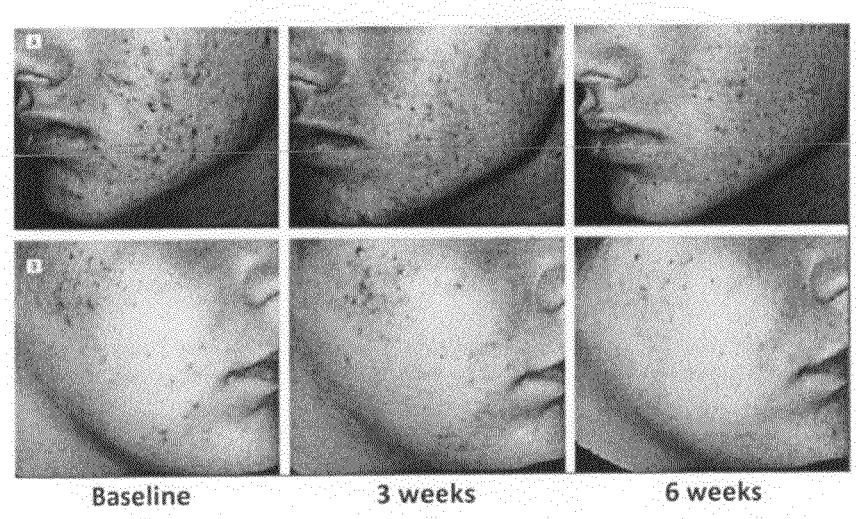
FIG. 4 are photographs of the facial skin of individual patients who participated in a clinical trial of the solubilized small molecule agent topical formulation.
Figure 5:
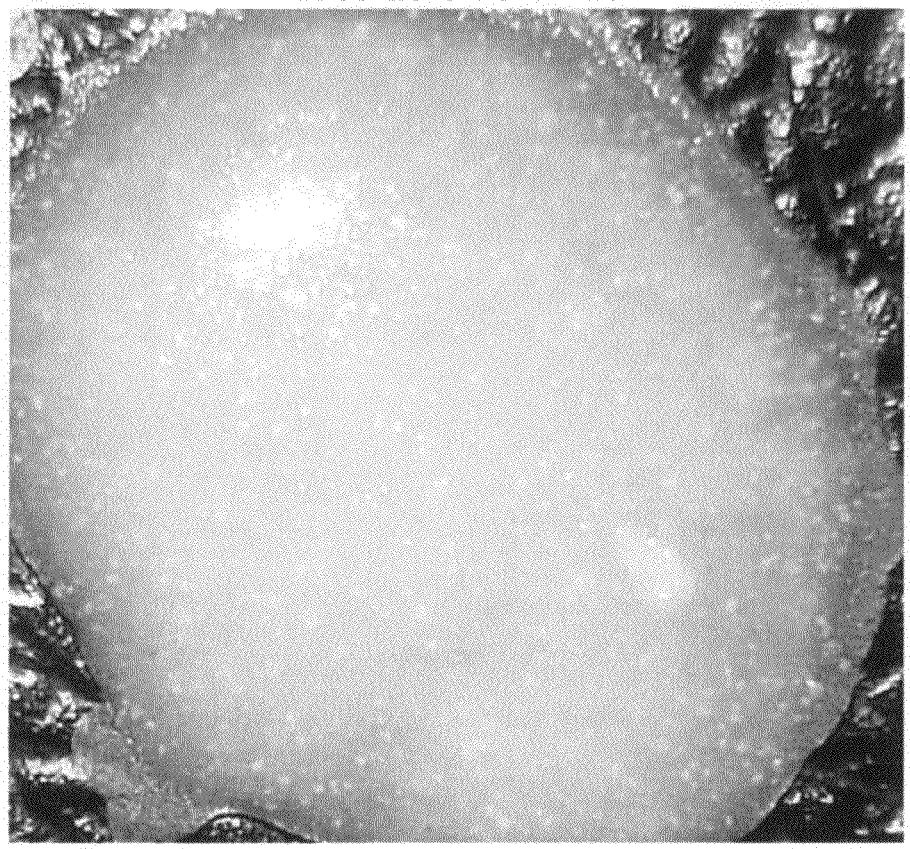
FIG. 5 shows a prior art unsolubilized small molecule agent (gritty topical formulation) on human skin at a magnification of 500× and FIG. 6 shows solubilized small agent in accordance with the invention
Figure 6:
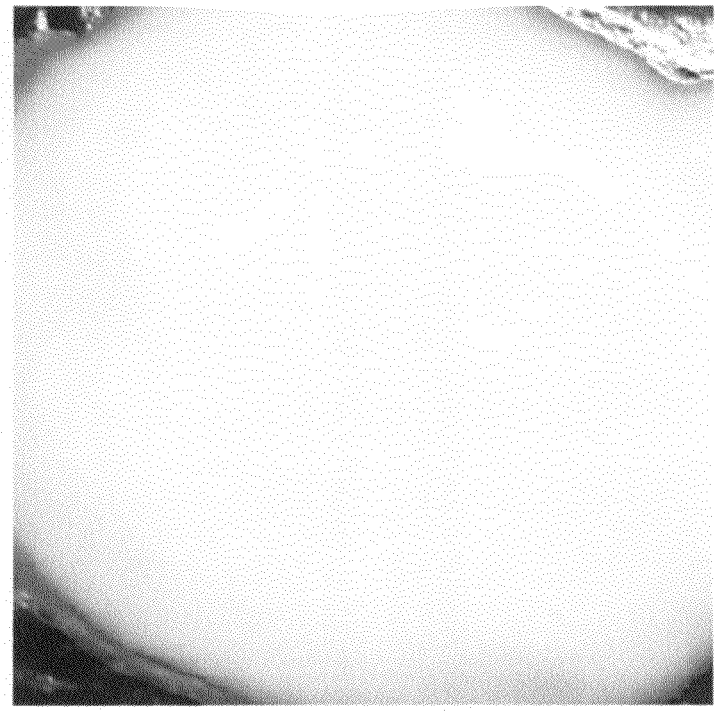

Results:

FIGS. 3 to 6 are representative before and after treatment photos of study participants. FIGS. 3a, 4a, 5a and 6a are before treatment photos of study participants. FIGS. 3b, 4b, 5b and 6b are post-treatment photos of patients following 12 weeks of treatment with the topical formulation of Example 1 (at 3.5% benzoyl peroxide).

Conclusion:

The 3.5% solubilized benzoyl peroxide topical formulation of Example 1 was found to be a safe and effective new method of acne treatment.

Example 5

Formulation with Lidocaine in it as an anesthetic agent.
RELOVOX Rx Repairing Lotion

| | |
|---|---|
| WATER, RO | 79.30000 |
| CARBOPOL ULTREZ 10 | 0.300000 |
| Xanthan Gum Norm, Fine | 0.150000 |
| Versene Na2 Crystal (45.36 KG DRUM) | 0.100000 |
| Tayl-Glycerine 99% U.S.P. | 4.000000 |
| Cithrol GMS A/S | 4.000000 |

-continued

| | |
|---|---|
| Crodacol CS-50 | 2.000000 |
| Cosmowax P | 1.000000 |
| Allantoin | 0.500000 |
| Lidocaine Hydrochloride | 1.00000 |
| DL-Panthenol 50% Liquid | 0.500000 |
| Germaben II-E | 0.700000 |
| TRIETHANOLAMINE 99% NF | 0.600000 |
| COLLOIDAL SULFUR | 1.000000 |
| Coastal Grapefruit 61-05-949 | 0.200000 |
| PEG-400/JEECHEM 400 NF | 5.000000 |
| BUTYLENE GLYCOL | 5.000000 |
| Ethanol 96%, Undenatured | 0.500000 |
| SODIUM LAURYL SULFATE, Stepanol WAC | 0.075000 |
| Sodium Hydroxide Soln. 50% (NF) | 0.075000 |
| BENZOYL PEROXIDE 97% | 3.000000 |

Numerous modifications, variations and adaptations may be made to the particular embodiments of the invention described above, without departing from the scope of the invention, which is defined in the following claims.

I claim:

1. A low temperature formed solubilized benzoyl peroxide topical formulation comprising:
   benzoyl peroxide in a concentration of between 1-10% by weight and not subjected to heating;
   one or more micelle forming compounds;
   one or more solvents maintained at 25 to 40 degrees C. selected from a group of pharmaceutically acceptable, organic solvents with a low dielectric constant, wherein said benzoyl peroxide is substantially dissolved in the organic solvent with a low dielectric constant;
   one or more skin penetration enhancers maintained at 25 to 40 degrees C.;
   a surfactant maintained at 25 to 40 degrees C.; and
   wherein said formulation is not subjected to any heating during processing and said formulation is stable at room temperature for a period in excess of four (4) weeks.

2. The solubilized benzoyl peroxide topical formulation of claim 1 wherein the one or more micelle forming compounds is selected from: lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof.

3. The solubilized benzoyl peroxide topical formulation of claim 1 wherein the one or more micelle forming compounds is present in the composition in a concentration of between about 1 and 20 wt./wt. % of the total composition.

4. The solubilized benzoyl peroxide topical formulation of claim 1 wherein the one or more micelle forming compounds is present in a concentration of between about 1 and 5 wt./wt. % of the total composition.

5. The solubilized benzoyl peroxide topical formulation of claim 1 further comprising an alkali metal alkyl sulfate which functions as a micelle forming agent, and is added to the composition in addition to the one or more other micelle-forming compounds.

6. The solubilized benzoyl peroxide topical formulation of claim 5 wherein the total concentration of said alkali metal alkyl sulfate edetate and said micelle-forming compounds together is less than 50 wt./wt. % of the total composition.

7. The solubilized benzoyl peroxide topical formulation of claim 2 wherein the lecithin can be saturated or unsaturated, and is preferably selected from the group consisting of phosphatidylcholine, phosphatidylserine, sphingomyelin, phosphatidylethanolamine, cephalin, and lysolecithin and mixtures thereof.

8. The solubilized benzoyl peroxide topical formulation of claim 2 wherein the salts of hyaluronic acid are alkali metal hyaluronates, selected from the group comprising sodium hyaluronate, alkaline earth hyaluronates, and aluminum hyaluronate.

9. The solubilized benzoyl peroxide topical formulation of claim 2 wherein the hyaluronic acid or pharmaceutically acceptable salts thereof are in a concentration of between about 1 and 5 wt./wt. % of the total composition is preferred, more preferably between about 1.5 and 3.5 wt./wt. %.

10. The solubilized benzoyl peroxide topical formulation of claim 1 wherein at least two micelle-forming compounds are used.

11. The solubilized benzoyl peroxide topical formulation of claim 10 wherein the micelle-forming compound combination is selected from the group consisting of i) sodium hyaluronate and saturated phospholipid, ii) lecithin and sodium hyaluronate, iii) sodium hyaluronate and evening of primrose oil, iv) saturated phospholipid and glycolic acid, v) saturated phospholipid, glycolic acid and lactic acid, vi) sodium hyaluronate, oleic acid and gamma linoleic acid, and vii) trihydroxy oxocholanyl glycine, lecithin and chenodeoxycholate.

12. The solubilized benzoyl peroxide topical formulation of claim 1 wherein the formulation has a pH in the range of 5 to 8.

13. The solubilized benzoyl peroxide topical formulation of claim 1 wherein the formulation has a pH in the range of 6 to 7.

14. The solubilized benzoyl peroxide topical formulation of claim 1 wherein the one or more solvents is selected from: ethylene glycol-400 (low molecular weight solvent), propylene glycol, butylene glycol, isopropyl alcohol, ethyl alcohol, short chain alkyl esters, ethers, aldehydes, ketones or alcohols of benzoic acid, benzyl alcohol, phenol or phathalic acid, aryl esters, ethers, alcohols of benzoic acid, benzyl alcohol, phenol, alkyl esters of benzoic acid, alkyl esters of benzyl alcohol, alkyl esters of salicylic acid, alkyl esters of phenol, alkyl esters of phthalic acid, alkyl ethers of benzyl alcohol, alkyl esters of phthalic acid, alkyl ethers of benzyl alcohol, alkyl ethers of phenol, benzoyl benzoate, benzoyl alcohol, diethyl phthalate, benzoic acid 2-phenyl ethyl ester, methyl salicylate, ethyl salicylate, propyl salicylate, butyl salicylate, ethyl benzoate, methyl benzoate, propyl benzoate, butyl benzoate, dimethyl phthalate, diethyl phthalate, benzyl ethyl ether, benzyl methyl ether, phenetole, phenyl acetone, phenyl ethyl alcohol, phenoxyethanol, phenyl acetaldehyde, ethyl phenyl acetate, phenyl methyl ketone, phenyl acetate, benzyl acetate, benzyl aceto acetate, benzyl formate, benzyl alcohol, ethyl benzyl alcohol, phenyl benzoate, phenyl ether, benzyl benzoate, and phenyl ethyl ester or combinations thereof.

15. The solubilized benzoyl peroxide topical formulation of claim 14 wherein the one or more solvents is selected from ethylene glycol-400 (low molecular weight solvent), propylene glycol, butylene glycol, isopropyl alcohol, ethyl alcohol, short chain alkyl esters, or combinations thereof.

16. The solubilized benzoyl peroxide topical formulation of claim 15 wherein the skin penetration enhancer is dimethylsulfoxide (DMSO).

17. The solubilized benzoyl peroxide topical formulation of claim 16 wherein the surfactant is sodium lauryl sulfate.

18. The solubilized benzoyl peroxide topical formulation of claim 17 wherein the small molecule agent is in a concentration of from 1 to 10% by weight.

19. The solubilized benzoyl peroxide topical formulation of claim 18 wherein the small molecule agent is in a concentration of from 2 to 5% by weight.

20. The solubilized benzoyl peroxide topical formulation of claim 19 wherein the solubilized small molecule agent topical formulation further comprises a topical anesthetic agent.

21. The solubilized benzoyl peroxide topical formulation of claim 20 wherein the solubilized small molecule agent topical formulation further comprises an antibiotic/bactericidal/antibacterial agent/antifungal agent.

22. The solubilized benzoyl peroxide topical formulation of claim 21 wherein the antibiotic/bactericidal/antibacterial agent is selected from: tetracylin and tetracyclin derivatives, gentamycin, kanamycin, streptomycin, neomycin, capreomycin, lineomycin, paromomycin, tobramycin, erythromycin, triclosan, antimicrobial peptides, octopirox, parachlorometa xylenol nystatin, tolnaftate, miconazole hydrochloride, chlorhexidine gluconate, chlorhexidin hydrochloride, methanamine hippurate, methanamine mandelate, minocycline hydrochloride, clindamycin, cleocin, 13-lactam derivatives such as aminopenicillin and mixtures thereof.

23. The solubilized benzoyl peroxide topical formulation of claim 19 that further comprises salicylic acid.

24. The solubilized benzoyl peroxide topical formulation of claim 19 that further comprises sodium hydroxide.

25. The solubilized benzoyl peroxide topical formulation of claim 19 that further comprises skin lightening agents or scar removing agents selected from a group comprising: hydroquinone, hydrogen peroxide, kombuchka, tri and pentatpetides, atrixyl and metrixyl 3000, witch hazel extract, grape seed extracts, green tea extracts, turmeric extracts in combination with sodium hyaluronate and collagen.

26. A process for the preparation of a solubilized benzoyl peroxide topical formulation, said process comprising:
 a. Combining one or more micelle forming compounds, one or more penetration enhancers, one or more solvents and surfactant at 25 to 40° C. with constant stirring;
 b. Adding small molecule agent powder to the foregoing solution; and
 c. Cooling the resultant solution to room temperature.

27. The process of claim 25 wherein the penetration enhancer is dimethylsulfoxide, the surfactant is sodium lauryl sulfate, and the solvent is selected from: ethylene glycol-400 (low molecular weight solvent), propylene or butylene glycol, isopropyl or ethyl alcohol, short chain alkyl esters, ethers, aldehydes, ketones or alcohols of benzoic acid, benzyl alcohol, phenol or phathalic acid, aryl esters, ethers, alcohols of benzoic acid, benzyl alcohol, phenol, alkyl esters of benzoic acid, alkyl esters of benzyl alcohol, alkyl esters of salicylic acid, alkyl esters of phenol, alkyl esters of phthalic acid, alkyl ethers of benzyl alcohol, alkyl esters of phthalic acid, alkyl ethers of benzyl alcohol, alkyl ethers of phenol, benzoyl benzoate, benzoyl alcohol, diethyl phthalate, benzoic acid 2-phenyl ethyl ester, methyl salicylate, ethyl salicylate, propyl salicylate, butyl salicylate, ethyl benzoate, methyl benzoate, propyl benzoate, butyl benzoate, dimethyl phthalate, diethyl phthalate, benzyl ethyl ether, benzyl methyl ether, phenetole, phenyl acetone, phenyl ethyl alcohol, phenoxyethanol, phenyl acetaldehyde, ethyl phenyl acetate, phenyl methyl ketone, phenyl acetate, benzyl acetate, benzyl aceto acetate, benzyl formate, benzyl alcohol, ethyl benzyl alcohol, phenyl benzoate, phenyl ether, benzyl benzoate, and phenyl ethyl ester or combinations thereof.

28. The process of claim 25 wherein at least one micelle-forming compound selected from the group comprising lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof.

29. The process of claim 26 wherein the at least one micelle-forming compound selected is present in the composition in a concentration of between about 1 and 20 wt./wt. % of the total composition.

30. The process of claim 26 wherein the at least one micelle-forming compound is present in a concentration of between about 1 and 5 wt./wt. % of the total composition.

31. The process of claim 25 wherein a second micelle forming agent is added to the composition in addition to the one or more other micelle-forming compounds listed set forth in claim 25.

32. The process of claim 25 further comprising skin lightening agents or scar removing agents from a group comprising: hydroquinone, hydrogen peroxide, kombuchka, tri and pentatpetides like atrixyl and metrixyl 3000, witch hazel extract, grape seed extracts, green tea extracts, turmeric extracts in combination with sodium hyaluronate and collagen.

33. The process of claim 25 wherein an alkali metal alkyl sulfate is added to the composition in addition to the one or more other micelle-forming compounds listed set forth in claim 25.

34. The solubilized benzoyl peroxide topical formulation of claim 1 wherein an isotonic agent is selected from the group consisting of glycerin or dibasic sodium phosphate and is added after formation of the mixed micellar composition.

* * * * *